United States Patent [19]

Wolsky et al.

[11] 4,256,912

[45] Mar. 17, 1981

[54] REMOVAL OF SOLUBLE TELLURIUM OR COMPOUNDS THEREOF FROM A CRUDE GLYCOL ESTER SOLUTION

[75] Inventors: Alfred A. Wolsky, Ft. Washington; Richard B. Papp, Norwood, both of Pa.; James G. Victor, Haddonfield, N.J.

[73] Assignee: Atlantic Richfield Company, Los Angeles, Calif.

[21] Appl. No.: 82,833

[22] Filed: Oct. 9, 1979

[51] Int. Cl.$^3$ .................. C07C 67/56; C07C 69/08; C07C 69/16; C07C 69/28
[52] U.S. Cl. .................. 560/248; 260/410.6; 260/550; 423/508; 423/509; 423/510; 560/246
[58] Field of Search .................. 560/248, 246; 260/410.6, 607 R; 423/508, 509, 510

[56] References Cited

U.S. PATENT DOCUMENTS

| | | | |
|---|---|---|---|
| 3,789,065 | 1/1974 | Kallar | 560/246 |
| 3,907,874 | 9/1975 | Harvey et al. | 560/246 |
| 4,045,477 | 8/1977 | Sherwin et al. | 560/246 |
| 4,073,876 | 2/1978 | Gupta | 560/246 |

*Primary Examiner*—Vivian Garner
*Attorney, Agent, or Firm*—Delbert E. McCaslin

[57] ABSTRACT

A method for the removal of soluble tellurium compounds from vicinal glycol ester solutions, prepared with tellurium-halide ion catalyst systems, by diluting the tellurium-containing vicinal glycol ester solution with water and contacting said glycol-water solution with a strongly acidic sulfonated ion exchange resin leaving an essentially tellurium-free vicinal glycol ester reaction product which may then be processed to recover the desired ester product and by-products without loss of valuable tellurium. The tellurium may be recovered from the ion exchange resin and treated to recover tellurium in a form suitable for reuse.

7 Claims, No Drawings

REMOVAL OF SOLUBLE TELLURIUM OR COMPOUNDS THEREOF FROM A CRUDE GLYCOL ESTER SOLUTION

BACKGROUND OF THE INVENTION

In U.S. Pat. Nos. 3,479,395, 3,637,515, 3,668,239, 3,689,535, 3,715,388, 3,715,389, 3,743,672, 3,789,065, 3,907,874, 3,985,795, 4,045,477 and 4,073,876 there are disclosed processes for the preparation of vicinal glycol esters by the liquid phase oxidation of an olefin, such as ethylene or propylene in a carboxylic acid medium, such as acetic acid using a tellurium catalyst and a source of halide ions.

The present invention is directed to an effective method of removing the tellurium from vicinal glycol ester solutions produced, for example, by such above described processes and containing tellurium in the form of soluble inorganic tellurium compounds and soluble organo-tellurium compounds. Because of the high reactivity of tellurium, in combination with a halide source when used as a catalyst as in the above reaction its combination with organic compounds such as the carboxylic acids and olefins employed very frequently results in the formation of organo-tellurium compounds, such as tetra and divalent alkyl tellurium halides, tellurium carboxylate compounds and the compounds described for example in an article by Jan Bergman, Kemisk Tedskrift, Vol. 88 (11), pp. 62-3, 1976, Sweden, entitled New Production Process for Ethylene Glycol as well as other soluble tellurium compounds which remain in solution with the glycol ester reaction product. In such reaction, a portion of the tellurium catalyst such as tellurium dioxide, etc. is itself or in combination with the halide source, converted to one or more organo-tellurium compounds. The type and number of organo-tellurium compounds which may be formed is a function of the reaction conditions to produce the vicinal glycol ester such as time, temperature, carboxylic acid and any solvent which might be employed. In addition, at least some of the inorganic tellurium compounds used as catalysts or formed in the reaction, such as tellurium tetrabromide, may also remain in solution with the glycol ester product.

Because of the cost and toxicity of tellurium, it is essential that as much of the tellurium be recovered from the glycol ester reaction product as is possible and from the inorganic or organo-tellurium compounds in a form suitable for reuse as a catalyst.

There is no known prior art which describes the removal of soluble inorganic or organo-tellurium compounds from a crude vicinal glycol ester reaction product, prepared by the tellurium catalyzed acetoxylation of olefins, by treating a water diluted solution of the glycol ester reaction product with a strongly acidic sulfonated ion exchange resin.

SUMMARY OF THE INVENTION

This invention relates to a process for the removal of tellurium from organic solutions containing soluble inorganic or organic tellurium compounds. More specifically, the present invention concerns a process for the treatment with a strongly acidic sulfonated ion exchange resin to remove soluble tellurium or compounds thereof from glycol ester solutions obtained from the tellurium catalyzed liquid phase reaction of an olefin, molecular oxygen and an aliphatic monocarboxylic acid in the presence of a halide ion as described for example in any of the aforementioned United States patents the processes of which are incorporated herein by reference. The crude vicinal glycol ester products produced by such processes, which may contain one or more soluble organo-tellurium compounds as well as soluble inorganic tellurium compounds, are percolated through, or intimately contacted with a strongly acidic sulfonated ion exchange resin to retain and remove the soluble tellurium compounds leaving an essentially tellurium-free vicinal glycol ester reaction product which may be processed to recover the ester product and by products, and any undesirable or unrecoverable material burned, if desired, for fuel value without loss of valuable tellurium. In a co-pending application Ser. No. 082,832 filed simultaneously herewith there is described a process for the removal and recovery of the tellurium retained on the ion exchange resin by elution with for example, dilute mineral acids. The tellurium enriched eluate acid solution may be subjected to stripping, distillation, extraction, etc., to remove water and recover acid, leaving a tellurium compound concentrate or residue which may be treated to recover the tellurium in a form suitable for reuse in the vicinal glycol ester synthesis reaction.

Advantages provided by the process of the present invention, are (1) it is an ion-exchange process and therefore not dependent upon differences in the relative volatilities of the tellurium and non-tellurium containing components of the vicinal glycol ester telluriumcontaining solutions as would be associated with possible distillation recovery methods and (2) there is no dependence upon relative solubilities of the tellurium and non-tellurium containing components as related to possible liquid-liquid extraction methods of recovery.

It is an object of this invention therefore to provide a method for the substantial removal of valuable tellurium from tellurium-containing vicinal glycol ester solutions and the ultimate purification of the glycol ester.

It is another object of this invention to provide a method for the removal of tellurium from vicinal glycol ester solutions and allow easy recovery of the tellurium for recycle and reuse as a catalyst for the synthesis of vicinal glycol esters by the liquid phase oxidation of an olefin in an aliphatic carboxylic acid medium.

It is a further object of this invention to recover contained tellurium values from tellurium-containing vicinal glycol ester solutions utilizing a strongly acidic sulfonated ion exchange resin to retain and remove the soluble tellurium compounds from the solutions.

These and other objects and advantages of this invention will become apparent from the description of the invention which follows and from the claims.

DETAILED DESCRIPTION OF THE INVENTION

In accordance with the present invention, a water diluted vicinal glycol ester solution containing soluble tellurium compounds, as for example, an ethylene glycol ester solution obtained by reacting under liquid phase oxidative conditions, ethylene, molecular oxygen and an aliphatic monocarboxylic acid such as acetic acid at a temperature of from about 80° C. to 200° C. in the presence of an effective amount of a tellurium catalyst such as tellurium dioxide in combination with a source of halide ions such as hydrobromic acid, is contacted with a strongly acidic sulfonated ion exchange resin by percolation of the tellurium-containing glycol ester solution through a bed of the resin or is intimately slurried with the resin to retain and remove the contained soluble tellurium compounds leaving an essentially tellurium free vicinal glycol ester reaction product which may then be processed by conventional methods to recover the desired vicinal glycol ester product and by-products. The ion exchange resin which retains the tellurium compounds may then be subjected to further treatments to elute the tellurium compounds from the ion exchange resin and form a tellurium-containing eluate solution.

Tellurium per se, which may be present in the crude vicinal glycol ester reaction product is essentially insoluble and may be and is preferably recovered, along with any other insoluble tellurium compounds, by filtration prior to treatment of the reaction product with the ion exchange resin to remove the soluble tellurium compounds.

The amount and type of tellurium compounds in the crude vicinal glycol ester reaction product will generally depend on the type and amount of tellurium compound and halide ion source employed to produce the glycol ester as well as the reaction conditions and ester being produced. Thus the amount of soluble tellurium in the form of inorganic tellurium compounds and/or organo-tellurium compounds can range from about 0.25 percent to 1.5 percent or more by weight of the glycol ester produced, for example by the processes as set forth in U.S. Pat. Nos. 3,668,239 and 3,715,389 noted above.

The removal of the soluble tellurium compounds with the sulfonated ion exchange resin is dependent upon the addition of water to the vicinal glycol ester reaction product solution prior to treatment. The product solution, which may already contain a small amount of water resulting from the oxidation reaction to prepare same is generally diluted on a weight basis with at least about 50 percent water and preferably 80 percent water giving an 80:20 percent by weight water-reaction product (oxidate) solution. While lesser concentrations of water could be employed a marked decrease in tellurium retention by the ion exchange resin results. In addition, it has been discovered that when substantial quantities of neat oxidate solutions are employed little if any of the contained soluble tellurium compounds are retained or removed by the ion exchange resin. Higher water concentrations, e.g., up to +99 percent may also be employed but is avoided since there is no apparent advantage, and accordingly, would only necessitate the handling of larger volumes of water along with the product ester affecting the process economics.

The strongly acidic sulfonated ion exchange resins (sold for example, commercially as "Amberlyst 15" a strongly acidic sulfonated poly aromatic ion exchange resin by Rohm and Haas Co.) and suitable for use in the present invention generally have a bulk density of approximately 595 g./l., a hydrogen ion concentration of approximately 4.9 milliequivalents/g. dry, a surface area of from about 40 to 50 m²/g. and an average pore diameter of from about 200 to 600 Angstrom units. Strongly acidic perfluoroalkane sulfonic acid resins (sold, for example, commercially as "Nafion" by the DuPont Co.) may also be employed and generally have an equivalent weight of between about 1000 and 1500, a hydrogen ion concentration of between about 0.7–1.0 milliequivalents/g. dry, and prepared, for example, by polymerization of tetrafluoroethylene with a sulfonyl fluoride vinyl ether, followed by saponification with caustic to form the alkali metal salt and treatment with an acid to convert the salt to the sulfonic acid form. Although not necessary to the process of the invention, the ion exchange resins when used in bed or columnar application if not already water swelled or conditioned, but are in the dry state, are preferably water swelled to prevent undue expansion of the bed during treatment of the tellurium-containing glycol ester.

Carboxylic acids such as acetic acid are employed to prepare the vicinal glycol esters along with the tellurium catalyst systems and are used as solvent as well as to supply the moiety for the subsequent ester produced. Separation or removal of the soluble tellurium compounds by employing the strongly acidic sulfonated ion exchange resins according to the present invention is not dependent upon the concentration of said carboxylic acid which may be present as one of the major components of the vicinal glycol ester reaction product solution.

The process of this invention may be carried out at temperatures of from about ambient to temperatures of about 95° C. and are preferably carried out between about 15° C. and 30° C. Higher or lower temperatures may be employed but are limited by the volatility of the lowest boiling components in the reaction solution to be treated and the freezing point of the reaction product solution with water or the temperature at which the viscosity increase inhibits proper flow through a bed or intimate mixture with the strongly acidic sulfonated ion exchange resin.

After the crude tellurium compound containing vicinal glycol ester solution has been treated by the process of the instant invention to essentially remove the soluble tellurium compounds and separated therefrom it may be processed by any known method to recover the desired ester product. The ion exchange resin may then be treated to recover the valuable tellurium and the resin and tellurium reactivated and recovered for reuse.

Although the process of the present invention will be directed to the treatment for removal of soluble tellurium compounds from a crude ethylene glycol diacetate solution containing tellurium compounds as well as other by-products and unreacted components and produced by the liquid phase oxidation of ethylene and acetic acid with molecular oxygen in the presence of tellurium dioxide and hydrobromic acid as set forth in U.S. Pat. No. 3,715,389, it is not intended that the process be limited to such ethylene glycol diacetate solution and those skilled in the art will recognize that the present invention is broadly applicable to the treatment of other tellurium-containing vicinal glycol ester solutions such as ethylene glycol diformate, dipropionate, dibutyrate, diisobutyrate, etc. as well as the propylene glycol diesters, 2,3-butanediol diesters, etc. which have been prepared, for example, by the tellurium catalyzed processes as described in the above noted U.S. patents.

The following Examples are provided to illustrate the removal of soluble tellurium compounds from a crude vicinal glycol ester solution in accordance with the principles of this invention but are not to be construed as limiting the invention in any way except as indicated by the claims.

In the Examples which follow, the reaction product ethylene glycol diacetate solution was obtained by taking the effluent from a tellurium oxide catalyzed conversion of ethylene with acetic acid, hydrobromic acid, 2-bromoethyl acetate and oxygen as described in U.S. Pat. No. 3,715,389.

EXAMPLE 1

20 grams of the reaction effluent ethylene glycol diacetate oxidate solution containing approximately 61.6 percent acetate and formate esters of ethylene glycol and diethylene glycol, 0.8 percent hydrobromic acid, 1.2 percent bromoacetic acid, 0.6 percent total tellurium as soluble tellurium compounds, 5.0 percent water, 24.8 percent acetic acid and 6.0 percent unidentified high molecular weight by-product material was diluted with 80 grams of water and centrifuged to separate any solid materials. The supernatant liquid containing the soluble tellurium was percolated through an 0.5 inch diameter glass column containing 25 ml of water conditioned strongly acidic sulfonated ion exchange resin ("Amberlyst 15" of Rohm and Haas Co.). Atomic absorption analysis of the treated effluent showed that >97 percent of the tellurium contained in the oxidate solution was retained and removed by the ion exchange resin. Repeated washings with water (>5 bed volumes) did not remove tellurium.

EXAMPLE 2

20 grams of reaction effluent ethylene glycol diacetate oxidate solution containing approximately 61.9 percent acetate and formate esters of ethylene glycol and diethylene glycol, 1.0 percent hydrobromic acid, 1.0 percent bromoacetic acid, 0.4 percent total tellurium as soluble tellurium compounds, 5.0 percent water, 24.7 percent acetic acid and 6.0 percent unidentified high molecular weight by-product material was diluted with 80 grams of water and filtered to remove insoluble components. 734 grams of filtrate containing 0.0856 percent (0.6285 grams) total tellurium was percolated through 25 ml. of water swelled strongly acidic sulfonated ion exchange resin ("Amberlyst 15") at an elution rate of 1.5 ml/minute and fractions of effluent taken and analyzed by atomic absorption for tellurium content. A total of 0.598 grams of tellurium was retained and removed from the glycol ester solution by the resin showing a capacity of approximately 1 gram of tellurium/15 grams of dry resin. The effluent data and analytical results are summarized in Table 1.

TABLE 1

Effluent Data: Through 25 ml resin-fixed bed-water swelled

| Fracton # | Wt. Grams | PPM Te in Effluent | Wt. Te (Milligrams) | % of Charge Te not retained in resin |
|---|---|---|---|---|
| #1 | 38.95 | 4.1 | 0.161 | 0.5 |
| #2 | 55.74 | 9.9 | 0.554 | 1.2 |
| #3 | 51.52 | 13.3 | 0.683 | 1.6 |
| #4 | 53.73 | 15.7 | 0.845 | 1.9 |
| #5 | 57.45 | 20.7 | 1.189 | 2.5 |
| #6 | 58.22 | 28.2 | 1.642 | 3.4 |
| #7 | 45.38 | 35.6 | 1.612 | 4.3 |
| #8 | 31.93 | 39.7 | 1.268 | 4.8 |
| #9 | 58.93 | 44.7 | 2.634 | 5.4 |
| #10 | 58.09 | 53.0 | 3.078 | 6.4 |
| #11 | 56.45 | 65.4 | 3.692 | 7.9 |
| #12 | 63.11 | 77.0 | 4.859 | 9.3 |
| #13 | 59.59 | 95.2 | 5.674 | 11.5 |
| #14 | 49.19 | 49.7 | 2.440 | 6.0 |
| #15 | 34.72 | 5.8 | 0.201 | 0.7 |
| Total | 773.00* | | 30.53 (.0305 grams) | |

Total Te Charged = .6285 grams
Total Te in effluent = .0305 grams
Total Te retained by resin = .5980 trams
*Includes 39 grams of water added after addition of filtrate solution to clear resin bed void volume.

EXAMPLE 3 (Comparative)

Example No. 1 was repeated employing 20 grams of an undiluted (neat) oxidate solution of the crude ethylene glycol diacetate which was filtered to remove insoluble components. Analysis by atomic absorption showed that only 42 percent of the total contained tellurium was removed or retained by the resin. An additional 20 grams of (neat) oxidate solution percolated through the bed failed to remove any tellurium from the oxidate solution.

EXAMPLE 4 (Comparative)

Example 1 was repeated employing 20 grams of the reaction effluent ethylene glycol diacetate oxidate solution which was diluted with 20 grams of water. The supernatant liquid after centrifugation was percolated through the resin bed at an elution rate of 1.5 ml./minute. Atomic absorption analysis of the resin treated effluent showed that only 53 percent of the total contained tellurium in the oxidate solution was retained or removed by the ion exchange resin.

EXAMPLE 5

20 grams of the reaction effluent ethylene glycol diacetate oxidate solution of Example 2 was diluted with 80 grams of water and centrifuged to remove solid components. The supernatant liquid containing the soluble tellurium was percolated through 25 ml of water swelled strongly acidic sulfonated resin ("Nafion" of the DuPont Co.—a strongly acidic perfluoroalkane sulfonic acid resin) at an elution rate of 1.5 ml/minute. Atomic absorption analysis of the treated effluent showed that >96 percent of the tellurium contained in the oxidate solution was retained and removed by the resin.

We claim:

1. A method for the removal of soluble tellurium or compounds thereof from tellurium-containing vicinal glycol ester solutions derived from the tellurium catalyzed liquid phase reaction of an olefin, molecular oxygen and an aliphatic monocarboxylic acid in the presence of a halide ion source which comprises the steps of:
    diluting the tellurium-containing vicinal glycol ester solution with at least about 50 percent by weight water;
    contacting the dilute water-tellurium-containing glycol ester solution at a temperature in the range of about 15° C. to 95° C. with a strongly acidic sulfonated ion exchange resin to retain and remove tellurium or compounds thereof from said dilute glycol ester solution; and
    recovering an essentially tellurium-free vicinal glycol ester solution.

2. A method according to claim 1 wherein the vicinal glycol ester solution is an ethylene glycol ester solution.

3. A method according to claim 2 wherein the solution is an ethylene glycol diacetate solution.

4. A method according to claim 1 wherein the tellurium-containing vicinal glycol ester solution is diluted with about 80 percent by weight water.

5. A method according to claim 1 wherein the temperature is in the range of from about 15° C. to 30° C.

6. A method according to claim 1 wherein the strongly acidic sulfonated ion exchange resin is a perfluoroalkane sulfonic acid resin.

7. A method for the removal of soluble tellurium or compounds thereof from a tellurium-containing ethylene glycol diacetate solution derived from the tellurium catalyzed liquid phase reaction of ethylene, molecular oxygen and acetic acid in the presence of a bromide ion source which comprises the steps of:

diluting the tellurium-containing ethylene glycol diacetate solution with at least about 50 percent by weight water;

contacting the dilute water-tellurium-containing ethylene glycol diacetate solution at a temperature of from about 15° C. to 30° C. with a strongly acidic sulfonated ion exchange resin to retain and remove tellurium or compounds thereof from said dilute ethylene glycol diacetate solution; and recovering an essentially tellurium-free ethylene glycol diacetate solution.

* * * * *